United States Patent
Renner et al.

(10) Patent No.: US 9,624,141 B2
(45) Date of Patent: Apr. 18, 2017

(54) PROCESS FOR PRODUCING SHORT-CHAIN OLEFINS WITH PROLONGED CYCLE TIME

(71) Applicant: L'Air Liquide, Societe Anonyme Pour l'Etude et l'Exploitation des Procedes Georges Claude, Paris (FR)

(72) Inventors: Thomas Renner, Frankfurt am Main (DE); Frank Castillo-Welter, Friedrichsdorf (DE); Stephane Haag, Frankfurt am Main (DE); Martin Gorny, Eschborn (DE); Theis Ohlhaver, Frankfurt am Main (DE); Roberta Olindo, Frankfurt am Main (DE)

(73) Assignee: L'Air Liquide Société Anonyme Pour L'Étude Et L'Exploitation Des Procedes Georges Claude, Paris (FR)

( * ) Notice: Subject to any disclaimer, the term of this patent is extended or adjusted under 35 U.S.C. 154(b) by 165 days.

(21) Appl. No.: 14/399,980

(22) PCT Filed: May 6, 2013

(86) PCT No.: PCT/EP2013/059336
§ 371 (c)(1),
(2) Date: Nov. 10, 2014

(87) PCT Pub. No.: WO2013/167510
PCT Pub. Date: Nov. 14, 2013

(65) Prior Publication Data
US 2015/0099915 A1    Apr. 9, 2015

(30) Foreign Application Priority Data
May 11, 2012 (DE) .......... 10 2012 104 128

(51) Int. Cl.
C07C 1/22 (2006.01)
B01J 8/04 (2006.01)
C07C 1/20 (2006.01)

(52) U.S. Cl.
CPC .............. *C07C 1/22* (2013.01); *B01J 8/0453* (2013.01); *B01J 8/0492* (2013.01); *C07C 1/20* (2013.01); *C07C 2529/40* (2013.01); *Y02P 30/42* (2015.11)

(58) Field of Classification Search
CPC .... C07C 1/00; C07C 1/22; C07C 1/24; C07C 1/20; C07C 11/04; C07C 11/06;
(Continued)

(56) References Cited

U.S. PATENT DOCUMENTS

| 4,404,414 A | 9/1983 | Penick et al. |
| 8,444,940 B2 * | 5/2013 | Bach ................... C07C 1/20 422/618 |

(Continued)

FOREIGN PATENT DOCUMENTS

| EP | 0448000 A1 | 9/1991 |
| EP | 1289912 B1 | 3/2003 |

(Continued)

*Primary Examiner* — Sharon Pregler
(74) *Attorney, Agent, or Firm* — Justin K. Murray

(57) ABSTRACT

A process for producing short-chain olefins by conversion of oxygenates in a multi-stage fixed-bed reactor, in which the individual stages for reaction zones are covered with beds of a granular, form-selective zeolite catalyst and the feed mixture containing oxygenates is added distributed over the reaction stages. An increase of the availability of the fixed-bed reactor for the olefin production with the same or an increased yield of short-chain olefins is achieved in that one or more reaction zones are charged with a distinctly reduced
(Continued)

mass flow of the feed mixture containing oxygenates, wherein the reduced mass flow fraction is distributed over other reaction zones.

20 Claims, 1 Drawing Sheet

(58) Field of Classification Search
CPC ... C07C 2529/40; B01J 8/0453; B01J 8/0492; Y02P 30/42
USPC .............................. 585/638, 639, 640, 641
See application file for complete search history.

(56) References Cited

U.S. PATENT DOCUMENTS

| | | |
|---|---|---|
| 2003/0139635 A1 | 7/2003 | Hack et al. |
| 2010/0063337 A1 | 3/2010 | Bach et al. |
| 2011/0288358 A1 | 11/2011 | Buchold et al. |

FOREIGN PATENT DOCUMENTS

| | | |
|---|---|---|
| WO | WO 9615082 A1 | 5/1996 |
| WO | WO 0192190 A1 | 12/2001 |
| WO | WO 2007140844 A1 | 12/2007 |
| WO | WO 2010066339 A1 | 6/2010 |

* cited by examiner

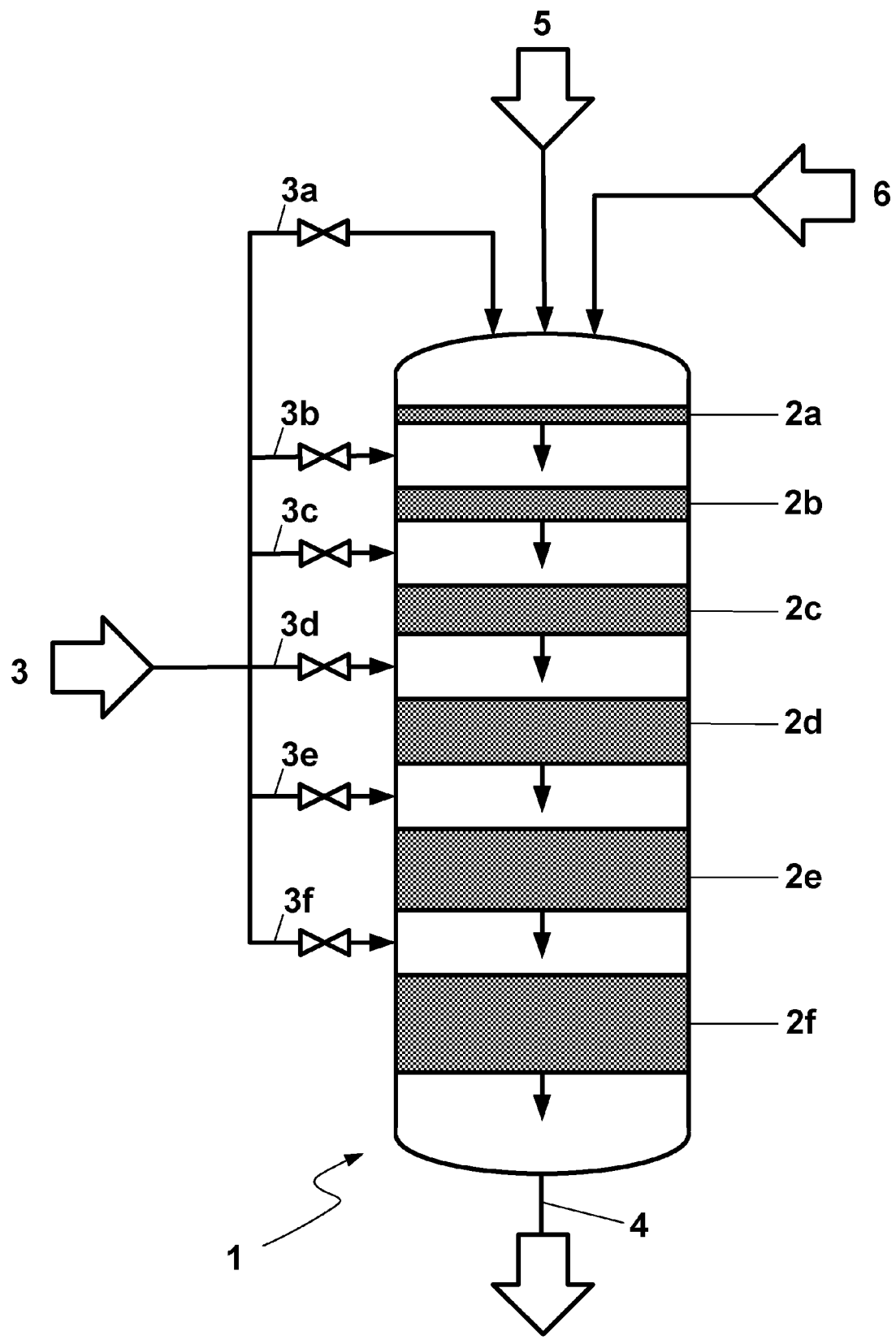

PROCESS FOR PRODUCING SHORT-CHAIN OLEFINS WITH PROLONGED CYCLE TIME

CROSS-REFERENCE TO PRIOR APPLICATIONS

This application is a U.S. National Stage application under 35 U.S.C. §371 of International Application No. PCT/EP2013/059336 filed on May 6, 2013, 20, and claims benefit to German Patent Application No. DE 10 2012 104 128.8 filed on May 11, 2012. The International Application was published in English on Nov. 14, 2013, as WO 2013/67510 A1 under PCT Article 21(2).

FIELD

This invention relates to a process for producing a hydrocarbon product containing short-chain, low-molecular olefins, in particular ethylene and propylene, by conversion of an educt mixture containing steam and oxygenates, for example methanol and/or dimethyl ether (DME), in a multi-stage fixed-bed reactor.

BACKGROUND

The production of hydrocarbon mixtures, in particular also of short-chain olefins, by conversion of oxygenates by using form-selective molecular sieve catalysts, in particular of pentasil zeolites of the structure type ZSM-5, is known from the prior art and described for example in the European Patent Application EP 0448000 A1 and the European Patent Specification EP 1289912 B1. The use of multi-stage fixed-bed reactors for this purpose also has been described already. For example, the International Patent Application WO 96/15082 A1 teaches a process for converting a feed mixture containing oxygenate compounds, for example methanol or dimethyl ether, into gasoline-like hydrocarbon compounds in a multi-stage fixed-bed process. In this process, fresh feed material containing oxygenates is supplied to a reaction zone together with the product gas from a preceding reaction zone and additional dilution gas. The temperature and composition of the dilution gas is chosen such that the increase in temperature in the exothermal reaction of the oxygenates to hydrocarbons in each of the succeeding reaction zones is limited to a maximum of 150° C., wherein the steam partial pressure should not exceed 2.2 ata. In this way, a premature deactivation of the zeolite catalyst used should be prevented, since too high a steam partial pressure at too high temperatures leads to an irreversible change in structure of the zeolite, with which catalytically active centers get lost. On the other hand, the steam is required as dilution medium and to prevent excessive carbon deposits on the catalyst. A slow deposition of carbon on the catalyst during the synthesis operation, however, is inevitable. When the same exceeds a tolerable maximum, the production operation must be interrupted and the carbon deposits must be removed for example by controlled burning off. The catalytic activity of the catalyst thereby can largely be restored, i.e. regenerated. The regeneration of the catalyst can be repeated several times, until the above-described irreversible deactivation has decreased the catalytic activity so much that a further use of the catalyst is prohibited for economic reasons. The time interval with production operation of the catalyst between two regenerations is referred to as cycle or also reaction cycle. The first cycle is the operating phase between the restart of the reactor with newly produced catalyst and the first regeneration.

The International Patent Application WO 2007/140844 A1 relates to a reactor for producing $C_2$ to $C_8$ olefins, preferably propylene, from a feed mixture comprising gaseous oxygenate, preferably dimethyl ether (DME) and/or methanol, steam and one or more of the hydrocarbons, which has a temperature of 400 to 470° C., and to a method for operating the reactor. The reactor contains a plurality of reaction stages or reaction zones arranged inside a closed upright container, which are traversed by the material stream from the top to the bottom, each consisting of a supporting tray with a fixed-bed zone located thereon, which is formed of a bed of granular molecular sieve catalyst. In a particular configuration, the reactor contains six reaction zones. Each supporting tray is constructed of cells firmly connected with each other, which are arranged one beside the other without spaces, and is suspended freely in the container. The cells are filled with a layer of molecular sieve catalyst. In the space defined by two adjacent reaction zones at the top and at the bottom, an atomizer system each is provided in the form of a number of nozzle tubes for uniformly spraying a liquid phase containing DME and/or methanol, chiefly consisting of steam and having a temperature of 25 to 150° C. by means of a gas phase saturated with water, chiefly containing DME and/or methanol and having a temperature of 170 to 300° C. towards the reaction stage following next in downstream direction. By spraying the liquid phase, the temperature of the reaction mixture exiting from the reaction stage with a temperature of 400 to 500° C. is lowered to a value of 380 to 470° C., so that the reaction proceeds in a narrow temperature range (quasi isothermally). The liquid phase can contain up to 30 vol-% of DME and/or methanol and the gas phase can contain up to 80 vol-% of DME and up to 30 vol-% of methanol.

For operating the reactor, a feed mixture containing gaseous oxygenate, preferably DME and/or methanol, as well as steam, which has a temperature of 150 to 300° C., is cooled to a temperature of 100 to 160° C., separated into a liquid phase and a gas phase, and liquid phase and gas phase are divided into several partial streams whose number each corresponds to the number of the spaces existing between the reaction stages. Based on a space, a gas-phase partial stream after heating to a temperature of 170 to 300° C. and a liquid-phase partial stream after cooling to a temperature of 25 to 150° C. each is supplied to an atomizer and sprayed into the space. By supplying gas and liquid in a corresponding temperature and quantity between the individual reaction stages, the inlet temperature of the reaction mixture exiting from the reaction stage into the space can be adjusted to the desired temperature before entry into the next following reaction stage.

The features of the reactor described in the document WO 2007/140844 A1 according to claims 1 to 13 as well as the features of the method for operating the reactor according to claims 14 to 15 and furthermore the description of an exemplary embodiment according to FIG. 1 to FIG. 7 and the associated description of Figures on p. 5 to p. 8 herewith are incorporated into the disclosure of the present patent application by reference.

The International Patent Application WO 2010066339 A1 teaches a process for producing a product containing propylene and ethylene by converting methanol and ethanol at the same time in an adiabatic reactor containing a plurality of series-connected reaction zones, wherein each reaction zone is covered with a fixed bed of form-selective catalyst, in that a feed mixture, comprising gaseous methanol, DME, steam and possibly one or more $C_2$, $C_4$, $C_5$, $C_6$, $C_7$, $C_8$ olefins and paraffins, is charged at least to the first reaction stage of the reactor at temperatures of 300 to 600° C. and pressures of 0.1 to 20 bar, absolute. By the distributed addition of the feed mixture containing oxygenates, advantages are achieved with regard to the temperature control and the suppression of undesired consecutive and side reactions.

With reference to the prior art discussed above, it can clearly be seen that so far it has been the primary objective to design the process of producing short-chain olefins from oxygenates by means of a multi-stage reactor such that optimum yields are obtained for the target products, i.e. in particular ethylene and propylene, with a good control of the exothermicity of the conversion reaction, since a maximization of the yield represents an important parameter for optimizing the process economy. What has been considered less, however, is the influence of the duration of the reaction cycles on the economy of the production process.

The catalyst life achieved so far with the production processes known from the prior art as described above is regarded as comparatively short—in particular with regard to the considerable price of the catalyst. Furthermore, several regenerations are required to achieve this previous maximum catalyst life.

Carrying out the regeneration between the various reaction cycles leads to a reduction of the operating period per reactor and per operating year and to an increased consumption of operating materials. This applies in particular to production plants which are operated outside an integrated association with ancillary facilities supplying operating materials. Carrying out each individual step of the regeneration procedure and transferring the reactor from the operating state into the regeneration mode and back binds a considerable part of the operating costs in the plant. In addition, the reactor is not available for the olefin production during the regeneration, so that the maintenance of a continuous production operation requires a multi strand concept for the production plant. Therefore, an increased catalyst life and an increase in the number of reaction cycles (tantamount to a reduced number of regenerations) would considerably improve the process economy of the production of short chain olefins from oxygenates.

SUMMARY

An aspect of the invention provides a process for producing a hydrocarbon product comprising ethylene and propylene, by converting a starting material mixture comprising steam and an oxygenate to one or more olefins under oxygenate conversion conditions in a reactor, the starting material mixture being divided into several partial streams, the process comprising: charging a first reaction zone of the reactor with steam and a first partial stream comprising the starting material mixture, the reactor comprising a plurality of series-connected reaction zones in fluid connection with each other, the reactor comprising a first reaction zone and at least one succeeding reaction zone; charging the at least one succeeding reaction zone with a second partial stream comprising the starting material mixture; and additionally charging each of the at least one succeeding reaction zone with a product stream from an upstream reaction zone; and further charging at least one of the at least one succeeding reaction zone with a reduced partial stream comprising the starting material mixture, wherein the reduced partial stream is smaller than a partial stream supplied to the upstream reaction zone.

BRIEF DESCRIPTION OF THE DRAWINGS

In the only FIGURE

FIG. 1 shows a schematic representation of an olefin synthesis reactor with six reaction zones in a longitudinal section as well as the position of the inlets of the educt mixture partial streams.

DETAILED DESCRIPTION

An aspect of the invention provides a process for producing short-chain, low-molecular olefins, such as ethylene and in particular propylene, from oxygenates such as methanol or DME, in which the length of the reaction cycles can be increased as compared to the processes known from the prior art, without suffering losses as regards the yields of the target products.

An aspect of the invention relates to a process for producing a hydrocarbon product containing short-chain, low-molecular olefins, in particular ethylene and propylene, by conversion of an educt mixture containing steam and oxygenates, for example methanol and/or dimethyl ether (DME), in a multi-stage fixed-bed reactor. The individual stages or reaction zones of the fixed-bed reactor may be covered with beds of a granular, form-selective zeolite catalyst. An aspect of the invention increases the availability of the fixed-bed reactor for the olefin production with the same or an increased yield of short-chain olefins, in particular of propylene (propene), as compared to previously known processes of the same type and thus increase the space-time yield of the reactor with regard to the olefins, in particular with regard to the propylene production.

An aspect of the invention provides a process for producing a hydrocarbon product containing olefins, comprising ethylene and propylene, by converting an educt mixture comprising steam and oxygenates, such as methanol and/or dimethyl ether, which is divided into several partial streams, to olefins under oxygenate conversion conditions in a reactor with a plurality of series-connected reaction zones which are in fluid connection with each other, comprising a first reaction zone and at least one succeeding reaction zone, wherein the first reaction zone is charged with an educt mixture partial stream and steam as well as optionally recirculation streams, and the succeeding reaction zones are charged with an educt mixture partial stream and the succeeding reaction zones additionally are charged with the product stream of the upstream reaction zone, which is characterized in that at least one of the succeeding reaction zones is charged with a reduced educt mixture partial stream which is smaller than the educt mixture partial stream supplied to the upstream reaction zone.

Fluid connection between two reaction zones is understood to be any kind of connection which enables a fluid, for example the feed stream, to flow from the one to the other of the two regions, regardless of any interposed regions or components.

Short-chain olefins in accordance with the present invention in particular are understood to be olefins which under ambient conditions are present in gaseous form, for example ethylene, propylene as well as the isomeric butenes 1-butene, cis-2-butene, trans-2-butene, iso-butene. Oxygenates are understood to be all oxygen-containing organic compounds which in the process according to the invention can be converted into olefins.

The conversion conditions required for the conversion of oxygenates to olefin products are known to the skilled person from the prior art, for example from the documents discussed above. Necessary adaptations of these conditions to the respective operating requirements will be made on the basis of routine experiments.

The idea underlying the present invention is based on varying the distribution of the educt mixture, i.e. the fresh oxygenate feed, to the catalyst zones of a multi-stage olefin synthesis fixed-bed reactor, in which all catalyst zones are filled with a catalyst active for the olefin synthesis from oxygenates, for example a ZSM-5 zeolite catalyst. For this purpose, the supply of the educt mixture is shifted from the last catalyst zones towards the front catalyst zones and thus the uniform distribution of the educt mixture partial streams, as it is taught in the prior art, is eliminated. Accordingly, the loading of the front catalyst zones with fresh oxygenate feed is significantly higher and the effective time of contact with the oxygenate feed is reduced. One or more of the succeeding catalyst zones are charged with a significantly reduced educt mixture partial stream. In the extreme case, for example, the last catalyst zone in flow direction is not charged with fresh feed, but only with the product stream of the upstream catalyst bed.

It has been found that with this new supply of the educt mixture not only the methanol conversion is increased, but also the propylene yield is not negatively influenced. The methanol conversion is connected with the duration of a reaction cycle such that as the end of a reaction cycle that point in time is defined at which a predefined minimum methanol conversion is reached or fallen short of. When reaching this point in time, it is necessary to transfer the reactor into the regeneration mode. These findings are surprising and in contrast with the expectation of the skilled person, according to which a rather uniform distribution of the educt mixture to all catalyst zones should lead to a uniform load of the catalyst and thus also to a uniform deactivation of the catalyst beds incorporated in the individual zones.

The increased methanol conversion observed when supplying the educt mixture according to the invention allows to extend the duration of the production operation per reaction cycle, before a regeneration becomes necessary. Accordingly, the frequency of the required regenerations is reduced. Surprisingly, it has been observed that the total amount of carbon deposited in the reactor remains approximately constant despite a changed supply of the educt mixture. Therefore, the same regeneration procedure can be employed, and the duration and costs per regeneration remain unchanged. Hence it follows that the influence of the regeneration costs on the produced ton of product, for example propylene, is decreased by the application of the process according to the invention.

The reduced amount of regeneration cycles per year of operating period simplifies the plant operation, since the procedures for the transfer of the reactors from the production operation into the regeneration mode and back must be performed less often. This also has additional advantages with regard to the service life of the catalyst used, since the performance of each regeneration is connected with a thermal load which leads to an irreversible deactivation—on a minor scale per regeneration. Since the irreversible deactivation of the catalyst ultimately determines its useful life, i.e. the possible operating period up to the necessary replacement of the catalyst filling of the synthesis reactor, the extended duration of the reaction cycles consequently also leads to an extension of the catalyst life.

In principle, the effect described above can be caused in that by charging with a reduced educt mixture partial stream, the space velocity in the corresponding catalyst zone or zones is reduced considerably as compared to the catalyst zones arranged further upstream. A particularly large effect is obtained when the corresponding educt mixture partial stream or streams not only are reduced, but decreased to zero.

The change of the supply of the educt mixture according to the invention advantageously also can be used to postpone the end of a reaction cycle or extend the reaction cycle, if no regeneration can be performed at a particular time for operational reasons. Examples can be the missing operability of a parallel reactor, for example because of a replacement of the catalyst in the latter, as well as a lack of availability of operating materials for an upcoming regeneration. For this purpose, a switch is made from a uniform distribution of the educt mixture partial streams to the changed supply of feed Preferably, the process according to the invention is carried out such that the reduced educt mixture partial stream is not more than 70%, preferably not more than 50% of the next larger educt mixture partial stream. As compared to a lower reduction, larger effects and advantages in terms of the extension of a reaction cycle are obtained in this way.

A particularly distinct extension of the reaction cycle is observed when in the process according to the invention the educt mixture partial stream supplied to the last reaction zone of the olefin synthesis reactor in flow direction not only is reduced, but decreased to zero. In addition, an educt mixture partial stream reduced for example to 50% or more optionally can be supplied to a reaction zone arranged further upstream.

In a preferred aspect of the process according to the invention, at least one recirculation stream additionally is supplied to the first and/or at least one succeeding reaction zone, which is obtained in the further processing of the reactor product. Water for example can serve as recirculation stream, which has been obtained from the product stream of the olefin synthesis reactor by condensation and optionally has been subjected to an aftertreatment. Furthermore, hydrocarbon streams, which are obtained in the course of the processing of the reactor product of the olefin synthesis reactor, also can partly be recirculated to the latter. As a result, the components contained therein, such as for example higher olefins like butenes, pentenes, hexenes, heptenes or octenes, additionally can be converted to ethylene and propylene, whereby the yield rises for these target products. In all cases, the temperature control of the olefin synthesis reactor is improved by charging the same with recirculation streams.

In a particularly preferred aspect, the olefin synthesis reactor contains six reaction zones; thus, a first and five succeeding reaction zones are provided. Sufficient operating experience already exists with this reactor construction (see the document WO 2007/140844 A1 discussed above), so that the process according to the invention can be applied particularly easily and its advantages as compared to the operation with uniformly distributed supply of the educt mixture partial streams can be recognized particularly clearly. This is the case in particular when no educt mixture partial stream is supplied to the sixth reaction zone in flow direction, but the same only is charged with the product stream of the upstream catalyst zone.

An advantageous aspect of the process according to the invention provides that an educt mixture partial stream added to a succeeding reaction zone is reduced from an initial value to a final value, with the reduced fraction being distributed to the other educt mixture partial streams, whereby the mass flow of the educt mixture supplied to the reactor remains constant overall. Due to the increased methanol conversion with constant selectivity to the target products, the yield of these target products thus can be increased further beside the extension of the reaction cycle.

In an alternative aspect of the process according to the invention it is provided that an educt mixture partial stream added to a succeeding reaction zone is reduced from an initial value to a final value, without the reduced fraction being distributed to the other educt mixture partial streams, whereby the mass flow of the educt mixture supplied to the reactor overall is reduced by this reduced fraction. This aspect for example can be utilized when switching from the synthesis operation into the regeneration mode. In this case, when the load of the upstream reaction zones is not changed, but the educt mixture partial stream, which is added to the succeeding reaction zone or zones, is reduced, a reduced total feed quantity of the educt mixture supplied to the reactor is obtained, which results in a lower propylene production, but a higher propylene yield relative to the feed quantity.

It was found to be particularly favorable that the conversion in the olefin synthesis reactor is carried out at temperatures of 300 to 600° C., preferably at temperatures of 360 to 550° C., most preferably at temperatures of 400 to 500° C., and at pressures of 0.1 to 20 bar, absolute, preferably at pressures of 0.5 to 5 bar, absolute, most preferably at pressures of 1 to 3 bar, absolute. The previous studies have shown that under these operating conditions particular advantages are obtained with regard to the yield of target products as well as the duration of the reaction cycles.

In principle, the invention can be utilized with all types of catalyst which are active for the conversion of oxygenates to olefins. Particular advantages are obtained, however, when the reaction zones contain a granular, form-selective zeolite catalyst of the pentasil type, preferably ZSM-5, in the form of a fixed bed. Suitable catalysts of this type are commercially available.

Further developments, advantages and possible applications of the invention can also be taken from the following description of exemplary embodiments and numerical examples and the drawings. All features described and/or illustrated form the invention per se or in any combination, independent of their inclusion in the claims or their back-reference.

In the olefin synthesis reactor 1 schematically shown in FIG. 1 a total of six reaction zones 2a to 2f are provided, which contain a bed of granular, commercially available catalyst. The catalyst is a ZSM-5-based zeolite active for the conversion of oxygenates such as methanol and DME to short-chain olefins, which can be obtained for example from Süd-Chemie AG under the designation MTPROP®. Details of the arrangement of the catalyst in the reactor and of the operation of the reactor can be found in the document WO 2007/140844 A1 already mentioned above. The suitable conversion conditions of said oxygenates to short-chain olefins also are mentioned in the last-mentioned WO publication; they are also known in principle to the skilled person and can be determined for the specific reaction conditions and the catalyst used by means of routine experiments. In doing so, care should be taken that a rather complete methanol conversion is achieved at a catalyst temperature which is not too high. In this way, an optimum result is obtained with regard to high methanol conversions, high yields of short-chain olefins and a long catalyst life.

In the embodiment shown in FIG. 1, the catalyst volume per reaction zone increases in flow direction, in order to achieve an approximately constant value for the space velocity in each reaction zone, since the volumetric gas flow is increased by supplying the educt mixture partial streams step by step.

In the present exemplary embodiment, the educt mixture is divided into six partial streams, which are supplied to the individual reaction zones via conduits 3a to 3f. Via flow controllers for each supply conduit 3a to 3f, which are only indicated, but not shown in detail in FIG. 1, the division is effected such that the reaction zones are charged with educt mixture mass flows of equal size. The educt mixture partial stream is supplied to the first reaction zone via conduit 3a. The first reaction zone additionally is charged with a steam stream via conduit 5 and with one or more recirculation streams containing hydrocarbons via conduit 6. Before entry into the catalyst bed of the first reaction zone, all partial streams supplied are intermixed with suitable measures known to the skilled person.

The second reaction zone 2b, as well as the succeeding reaction zones 2c to 2f, each are charged with an educt mixture partial stream and in addition with the product stream leaving the upstream reaction zone; this is indicated in FIG. 1 by vertical flow arrows after the respective reaction zone. The supply of the educt mixture partial stream is effected via suitable distributor systems described in detail in WO 2007/140844 A1, in order to achieve a homogeneous distribution of the educt mixture over the reactor cross-section.

According to the invention, the last reaction zone 2f in flow direction is charged with an educt mixture partial stream via conduit 3f, whose mass flow is reduced distinctly, preferably by at least 50%, as compared to the educt mixture partial streams supplied upstream via conduits 3a to 3e. According to a particularly preferred aspect of the invention, the educt mixture partial stream in conduit 3f is zero, i.e. no fresh educt mixture is supplied to the reaction zone 2f. In this embodiment, the reaction zone 2f therefore serves as pure post-reaction zone.

Via conduit 4, the product mixture leaves the olefin synthesis reactor 1 and is supplied to the product processing known per se, which is described for example in the European Patent Application EP 0448000 A1 and the European Patent Specification EP 1289912 B1.

The following results were obtained in tests in a pilot plant, comprising an olefin synthesis reactor with six reaction zones according to FIG. 1. Under standard operating conditions, a total methanol mass flow of 1050 g/h was supplied to the reactor, wherein each individual catalyst bed (six catalyst beds in all) was loaded with a space velocity (WHSV) related to the catalyst mass of $0.71^{-1}$. In addition, the reactor was charged with a constant steam mass flow of 1000 g/h. The inlet temperature into the first catalyst bed of the olefin synthesis reactor was between 460 and 470° C. and the outlet temperature for all beds was about 480° C. The pressure at the reactor outlet was 1.3 bara. The catalyst quantity per catalyst bed was different, with the first catalyst bed having the smallest catalyst quantity and the catalyst quantity rising step by step in the downstream beds. The sixth and last catalyst bed accordingly contained the highest catalyst quantity. Consequently, the quantity of the educt mixture added to the individual catalyst beds also was rising. The test results obtained thereby are listed in the following Table.

During test phase 1, standard operating conditions were used (WHSV=0.7 $h^{-1}$ for each catalyst bed and a total quantity of 1050 g/h of methanol plus 1000 g/h of water). During test phases 2 and 3 on the other hand, the methanol supply to the reaction zone 6 (corresponds to 2f in FIG. 1) was stopped completely, i.e. the last, sixth catalyst bed only was charged with the product stream of the fifth, upstream catalyst bed. At the same time, the space velocity for the other catalyst beds 2a to 2e was uniformly increased from 0.7 $h^{-1}$ to 0.94 $h^{-1}$, in order to keep the mass flow of 1050 g/h of methanol to the entire reactor constant. Finally, during test phase 3 the space velocity for all catalyst beds, except for the last, again was reduced to 0.7 $h^{-1}$, wherein the last catalyst bed in turn only was charged with the product stream of the upstream catalyst stage. This corresponds to a reduction of the methanol mass flow to the reactor from 1050 to 780 g/h.

Test phases 1 to 3 were carried out in the time sequence corresponding to their numbering and without interposition of a catalyst regeneration.

TABLE

Conversion of methanol to propylene in a six-stage olefin synthesis reactor with distributed addition of the methanol feed

| Test phase | Total feed of MeOH g/h | MeOH to Rct. zone 6 g/h | Total run time h-o-s | Methanol conversion X(MeOH) to HC | Propylene yield[#] wt-% | Propylene production g/h |
|---|---|---|---|---|---|---|
| 1 | 1050 | 268.8 | 23 | 94.8% | 27.6 | 274.5 |
| 1 | 1050 | 268.8 | 35 | 94.3% | 27.3 | 270.5 |
| 1 | 1050 | 268.8 | 47 | 94.0% | 27.2 | 268.2 |
| 1 | 1050 | 268.8 | 59 | 92.9% | 27.2 | 264.6 |
| 1 | 1050 | 268.8 | 71 | 92.3% | 27.2 | 263.8 |
| 1 | 1050 | 268.8 | 83 | 91.3% | 27.4 | 264.1 |
| 1 | 1050 | 268.8 | 95 | 90.6% | 27.4 | 263.2 |
| Mean value | | | | 92.9% | 27.3 | 267.0 |
| 2 | 1050 | 0.0 | 107 | 94.5% | 27.4 | 269.3 |
| 2 | 1050 | 0.0 | 119 | 95.4% | 27.0 | 271.5 |
| 2 | 1050 | 0.0 | 131 | 94.8% | 28.1 | 279.5 |
| 2 | 1050 | 0.0 | 143 | 94.6% | 29.0 | 288.8 |
| 2 | 1050 | 0.0 | 155 | 93.7% | 28.6 | 281.9 |
| 2 | 1050 | 0.0 | 167 | 93.9% | 27.9 | 276.5 |
| 2 | 1050 | 0.0 | 179 | 93.4% | 28.4 | 279.6 |
| 2 | 1050 | 0.0 | 191 | 93.1% | 28.6 | 282.4 |
| Mean value | | | | 94.2% | 28.1 | 278.7 |
| 3 | 780 | 0.0 | 215 | 94.5% | 30.9 | 228.1 |
| 3 | 780 | 0.0 | 227 | 93.9% | 29.6 | 217.8 |
| 3 | 780 | 0.0 | 239 | 93.7% | 29.0 | 213.2 |
| 3 | 780 | 0.0 | 251 | 93.2% | 29.8 | 217.9 |
| 3 | 780 | 0.0 | 263 | 93.0% | 30.3 | 221.6 |
| 3 | 780 | 0.0 | 275 | 92.7% | 30.2 | 220.2 |
| 3 | 780 | 0.0 | 287 | 92.6% | 30.2 | 219.8 |
| Mean value | | | | 93.4% | 30.0 | 219.8 |

[#]Definition: g/h propylene/(g/h MeOH, in − (g/h MeOH, out + g/h DME, out))

With reference to the data shown in the Table it can be seen that switching from a uniform distribution of the methanol feed over all six reaction zones (test phase 1) to an operation in which only the first five reaction zones in flow direction (FIGS. 1, 2a to 2e) are charged with fresh methanol feed, and to the sixth reaction zone (FIGS. 1, 2f) merely the product stream leaving the fifth reaction zone (2e) is supplied (test phase 2), leads to a significant increase of the methanol conversion to hydrocarbon products and the propylene yield and hence also to the propylene production. In practice, this means that in operation by the process according to the invention the olefin synthesis reactor can be operated longer as compared to the operating conditions corresponding to test phase 1, until an admissible minimum methanol conversion is fallen short of and therefore a regeneration must be carried out.

When reducing the total methanol feed from 1050 to 780 g/h in test phase 3, a further increase of the propylene yield can be observed. But since less methanol is converted overall, the propylene production decreases distinctly. However, the propylene yield now is increased distinctly and roughly amounts to 30 wt-% as compared to 27.3 wt-% in test phase 1 and 28.1 wt-% in test phase 2. The test conditions during test phase 2, which correspond to a particularly preferred aspect of the process according to the invention, therefore represent an optimum with regard to a high propylene production with a prolonged cycle time at the same time.

With the invention, a process for producing short-chain olefins is proposed, which is characterized by a high yield of ethylene and in particular propylene with an extension of the cycle time at the same time and thus a reduced number of regenerations per catalyst charge. The application of the process according to the invention increases the flexibility with regard to the choice of the time for the regeneration operation.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS

[1] olefin synthesis reactor
[2a-2f] reaction zone
[3a-3f] conduit educt mixture partial stream
[4] conduit product
[5] conduit steam
[6] conduit recirculation stream

The invention claimed is:

1. A process for producing a hydrocarbon product comprising one or more olefins, by converting a starting material mixture comprising steam and an oxygenate to one or more olefins under oxygenate conversion conditions in a reactor, the process comprising the steps of:
   i) dividing the starting material mixture into a first partial stream, at least one succeeding partial stream, and a final partial stream;
   ii) charging a first reaction zone of the reactor with steam and the first partial stream, the reactor comprising a plurality of series-connected reaction zones in fluid connection with each other, the reactor comprising the first reaction zone, at least one succeeding reaction zone disposed downstream the first reaction zone, and a final reaction zone disposed downstream the at least one succeeding reaction zone;

iii) charging the at least one succeeding reaction zone with the at least one succeeding partial stream;
iv) additionally charging each of the at least one succeeding reaction zones and the last reaction zone with a product stream from an upstream reaction zone; and
v) further charging the final reaction zone with the final partial stream,
wherein the final partial stream comprises a mass flow rate smaller than a next larger partial stream selected from the group consisting of the first partial stream, the at least one succeeding partial stream, and combinations thereof.

2. The process of claim 1, wherein the final partial stream is not more than 70% of the next larger partial stream.

3. The process of claim 1, wherein the process of claim 1 operates according to a first mode, wherein the process may further comprise a second mode of operation, such that during the second mode of operation, the final partial stream charged to the final reaction zone during step v) has a mass flow rate of zero such that the final reaction zone receives no flow of the starting material mixture attributable to the final partial stream.

4. The process of claim 1, comprising:
supplying at least one recirculation stream to the first reaction zone, the at least one succeeding reaction zone, or a combination thereof,
wherein the at least one recirculation stream is obtained in further processing of a reactor product.

5. The process of claim 1, wherein the at least one succeeding reaction zone comprises a first succeeding reaction zone, a second succeeding reaction zone, a third succeeding reaction zone, and a fourth succeeding reaction zone.

6. The process of claim 1, comprising:
reducing the mass flow rate of the final partial stream charged during step v) by a first amount;
increasing the mass flow rate of at least one of the partial streams of steps ii) and iii) such that the overall mass flow of the starting material mixture supplied to the reactor is maintained constant.

7. The process of claim 1, comprising:
reducing the mass flow rate of the final partial stream charged during step v) by a first amount;
increasing the mass flow rate of at least one of the partial streams of steps ii) and iii) by a second amount that is lower than the first amount such that the overall mass flow of the starting material mixture supplied to the reactor is reduced.

8. The process of claim 1 wherein the converting is carried out in a temperature range from 300° C. to 600° C.

9. The process of claim 1, wherein the converting is carried out in a temperature range from 360° C. to 550° C.

10. The process of claim 1 wherein the converting is carried out in a pressure range from 0.1 bar to 20 bar, absolute.

11. The process of claim 1, wherein the converting is carried out in a pressure range from 0.5 bar to 5 bar, absolute.

12. The process of claim 1, wherein the converting is carried out in a pressure range from 1 bar to 3 bar, absolute.

13. The process of claim 1 wherein the reaction zones comprise a granular, form-selective zeolite catalyst of the pentasil type in the form of a fixed bed.

14. The process of claim 1, wherein the oxygenate comprises methanol, dimethyl ether, or both.

15. The process of claim 1, wherein the first reaction zone is additionally charged with at least one recirculation stream.

16. The process of claim 13, wherein the reaction zones comprise a ZSM-5 catalyst.

17. A process for producing a hydrocarbon product comprising one or more olefins, the process comprising the steps of:
converting a starting material mixture comprising steam and an oxygenate to one or more olefins under oxygenate conversion conditions in a reactor, the reactor comprising a plurality of series-connected reaction zones in fluid connection with each other, wherein each reaction zone produces a respective product stream,
wherein the step of converting the starting material mixture further comprises a first mode of operation having the steps of:
dividing the starting material mixture into a first partial stream, at least one intermediate partial stream, and a final partial stream;
charging a first reaction zone of the reactor with steam and the first partial stream, wherein the plurality of series-connected reaction zones comprise the first reaction zone, at least one intermediate reaction zone located downstream the first reaction zone, and a final reaction zone located downstream the at least one intermediate reaction zone;
charging the at least one intermediate reaction zone with the intermediate partial stream, wherein each of the at least one intermediate reaction zones is charged with the product stream from the reaction zone immediately upstream each intermediate reaction zone; and
charging the final reaction zone with the final partial stream, wherein the final partial stream has a mass flow rate smaller than the mass flow rate of a partial stream selected from the group consisting of the first partial stream, each of the at least one intermediate partial streams, and combinations thereof.

18. The process of claim 17, wherein the process comprises a second mode of operation having the steps of:
reducing the mass flow rate of the final partial stream charged to the final reaction zone by a first amount such that the mass flow rate of the final partial stream to the final reaction zone is zero; and
increasing the mass flow rate of a remaining partial stream by the first amount such that the total flow rate of starting material mixture remains constant for both the first mode and second mode of operation, wherein the remaining partial stream is selected from the group consisting of the first partial stream, each of the at least one intermediate partial streams, and combinations thereof.

19. The process of claim 17, wherein the process comprises a second mode of operation having the steps of:
reducing the mass flow rate of the final partial stream charged to the final reaction zone by a first amount such that the mass flow rate of the final partial stream to the final reaction zone is zero; and
increasing the mass flow rate of a remaining partial stream by the first amount such that the total flow rate of starting material mixture is higher in the first mode as compared to the second mode of operation, wherein the remaining partial stream is selected from the group consisting of the first partial stream, each of the at least one intermediate partial streams, and combinations thereof.

20. A process for producing a hydrocarbon product comprising one or more olefins, by converting a starting material mixture comprising steam and an oxygenate to one or more olefins under oxygenate conversion conditions in a reactor, the process comprising the steps of:
  i) dividing the starting material mixture into a first partial stream and at least one succeeding partial stream;
  ii) charging a first reaction zone of the reactor with steam and the first partial stream, the reactor comprising a plurality of series-connected reaction zones in fluid connection with each other, the reactor comprising the first reaction zone, at least one succeeding reaction zone disposed downstream the first reaction zone, and a final reaction zone disposed downstream the at least one succeeding reaction zone;
  iii) charging the at least one succeeding reaction zone with the at least one succeeding partial stream;
  vi) additionally charging each of the at least one succeeding reaction zones with a product stream from an upstream reaction zone; and
  vii) charging the final reaction zone with only a product stream from an upstream reaction zone such that the final reaction zone does not receive a direct flow of the starting material mixture.

* * * * *